United States Patent [19]

Umezawa et al.

[11] Patent Number: 4,486,419
[45] Date of Patent: Dec. 4, 1984

[54] 5,2',3',4',4'',6''-HEXADEOXYKANAMYCIN AND ITS 1-N-ACYLATED DERIVATIVE

[75] Inventors: Hamao Umezawa, Tokyo; Shinichi Kondo, Yokohama, both of Japan

[73] Assignee: Zaidan Hojin Biseibutsu Kagaku Kenkyu Kai, Japan

[21] Appl. No.: 532,058

[22] Filed: Sep. 14, 1983

[30] Foreign Application Priority Data

Sep. 20, 1982 [JP] Japan .................................. 57-162292

[51] Int. Cl.³ ........................ A61K 31/71; C07H 15/22
[52] U.S. Cl. .................................. 424/180; 536/13.6; 536/13.7; 536/13.8; 536/13.9
[58] Field of Search .................... 536/13.6, 13.7, 13.8, 536/13.9; 424/180

[56] References Cited

U.S. PATENT DOCUMENTS 4,298,727  11/1981  Umezawa et al. ................. 536/13.8
4,332,794   6/1982  Umezawa et al. ................. 536/13.7

FOREIGN PATENT DOCUMENTS 2724597  12/1977  Fed. Rep. of Germany ..... 536/13.7

*Primary Examiner*—Johnnie R. Brown
*Assistant Examiner*—Elli Peselev
*Attorney, Agent, or Firm*—Larson and Taylor

[57] ABSTRACT

5,2',3',4',4'',6''-Hexadeoxykanamycin and 1-N-[(S)-4-amino-2-hydroxybutyryl]-5,2',3',4',4'',6''-hexadeoxykanamycin are now provided, which are each a new compound useful as antibacterial agent. The hexadeoxykanamycin is semi-synthetically produced from 3',4'-dideoxykanamycin through consecutive steps which are ingeniously combined with each other to remove the 5-, 2'-, 4''- and 6''-hydroxyl groups. The 1-N-acylated hexadeoxykanamycin is produced by acylating the 1-amino group of hexadeoxykanamycin with (S)-4-amino-2-hydroxybutyric acid.

6 Claims, No Drawings

5,2',3',4',4'',6''-HEXADEOXYKANAMYCIN AND ITS 1-N-ACYLATED DERIVATIVE

This invention relates to 5,2',3',4',4'',6''-hexadeoxykanamycin and 1-N-(ω-amino-α-hydroxyalkanoyl)-5,2',3',4',4'',6''-hexadeoxykanamycin which are each new compound useful as semi-synthetic aminoglycosidic antibiotics. This invention also relates to processes for the production of these new compounds, as well as a pharmaceutical composition containing at least one of these new compounds as active ingredient.

We, the present inventors, have researched into the mechanism of resistance in bacteria to aminoglycosidic antibiotics, and on the basis of our researches in this respect we have succeeded to synthesize many deoxy-derivatives of kanamycin-group antibiotics which are active against bacterial strains which are resistant to kanamycins (see U.K. Patent Application GB No. 2082575 A). In particular, dibekacin (3',4'-dideoxykanamycin B; see Japanese Patent Publication No. 7595/75, Japanese Pat. No. 794,612, U.S. Pat. No. 3,753,973) synthesized by us is widely used in therapeutic treatment of bacterial infections. Habekacin (namely, 1-N-[(S)-4-amino-2-hydroxybutyryl] dibekacin; see Japanese Patent Publication No. 33629/77, U.S. Pat. No. 4,107,424) is clinically studied as a chemotherapeutic agent which is active against dibekacin-resistant bacteria. Now, we have made our further study in an attempt to provide a new polydeoxy-derivative of kanamycin which is active not only against the dibekacin-resistant bacteria but also against such habekacin-resistant bacteria which are expectable to occur in future owing to extensive use of dibekacin and habekacin in clinics.

As a result, we have now synthesized 5,2',3',4'-4'',6''-hexadeoxykanamycin (hereinafter sometimes abbreviated as the hexadeoxykanamycin) which contains only one hydroxyl group remaining at the 2''-position of the parent kanamycin A molecule and from which there have been removed the six hydroxyl groups initially existing at the 5-, 2'-, 3'-, 4'- and 4''- and 6''-positions of the parent kanamycin A molecule. We have now found that this hexadeoxykanamycin now synthesized is a new compound which exhibits antibacterial activity as high as that of the parent kanamycin A. We have further synthesized 1-N-[(S)-4-amino-2-hydroxybutyryl]-5,2',3',4',4'',6''-hexadeoxykanamycin (hereinafter sometimes abbreviated as hexadeoxyamikacin) from the hexadeoxykanamycin, and we have now confirmed that this hexadeoxyamikacin is a new compound which exhibits antibacterial activity as high as that of amikacin (namely, 1-N-[(S)-4-amino-2-hydroxybutyryl]kanamycin A; see U.S. Pat. No. 3,781,268) even with the kanamycin-resistant bacteria. Thus, we have accomplished this invention.

According to a first aspect of this invention, therefore, there is provided as a new compound 5,2',3',4',4'',6''-hexadeoxykanamycin or a 1-N-acyl derivative thereof represented by the general formula (I)

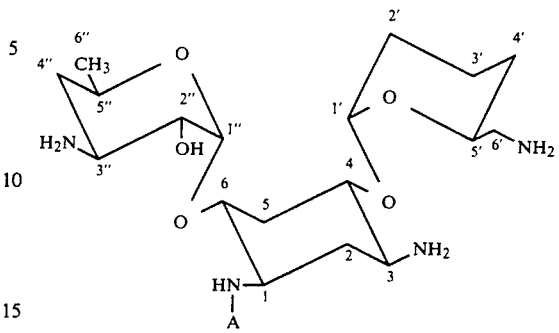

wherein A denotes a hydrogen atom or (S)-4-amino-2-hydroxybutyryl group, or an acid addition salt of the compound of the general formula (I).

The examples of the new compounds of the general formula (I) according to this invention are the undermentioned particular compounds of which physicochemical properties are as follows:

(1) 5,2',3',4',4'',6''-Hexadeoxykanamycin which is the compound of the general formula (I) where A is a hydrogen atom. This compound is obtained in the form of mono-carbonate mono-hydrate and as a colorless powder which does not show a definite melting point but decomposes at 191° to 196° C. and which shows a specific optical rotation $[\alpha]_D^{23} +103°$ (c 1, water). The elemental analysis gave the found values: C 48.95%, H 8.41%, N 11.71% which were coincident with the theoretical values of $C_{18}H_{36}N_4O_5 \cdot H_2CO_3 \cdot H_2O$ (C 48.70%, H 8.60%, N 11.96%). Mass spectrometry gave a value: m/z 388 (M+). The hexadeoxykanamycin gave a single spot (positive to ninhydrin) at Rf 0.47 and Rf 0.78, in silica gel thin layer chromatography when developed with butanol-ethanol-chloroform-17% aqueous ammonia (4:5:2:5 by volume) and with chloroform-methanol-conc. aqueous ammonia-water (1:4:2:1 by volume), respectively, as the development solvent.

The hexadeoxykanamycin shows the antibacterial spectrum as given in Table 1 later.

(2) 1-N-[(S)-4-Amino-2-hydroxybutyryl]-5,2',3',4',4'',6''-deoxykanamycin which is the compound of the general formula (I) where A is an (S)-4-amino-2-hydroxybutyryl group. This compound is obtained in the form of mono-carbonate di-hydrate and as a colorless powder which does not show a definite melting point but decomposes at 157° to 162° C. and shows a specific optical rotation $[\alpha]_D^{25} +61°$ (c 1, water). Its elemental analysis gave the found values: C 47.16%, H 8.13%, N 11.61% which were coincident with the theoretical values of $C_{22}H_{43}N_5O_7 \cdot H_2CO_3 \cdot 2H_2O$ (C 47.01%, H 8.40%, N 11.92%). Its mass spectrometry could not be observed but its chemical structure was supported by its nuclear magnetic resonance spectrum. The hexadeoxyamikacin gave a single spot (positive to ninhydrin) at Rf 0.31 and Rf 0.46 in silica gel thin layer chromatography when developed with butanolethanol-chloroform-17% aqueous ammonia (4:5:2:5 by volume) and with chloroform-methanol-conc. aqueous ammonia-water (1:4:2:1 by volume) as the development solvent, respectively. This hexadeoxyamikacin gave the antibacterial spectrum as shown in Table 1 below.

Thus, the minimum inhibitory concentrations (mcg/ml) of the hexadeoxykanamycin and of the hexadeoxyamikacin according to this invention against various microorganisms were determined according to serial dilution method on a nutrient agar medium at 37° C., the estimation being made after 18 hours incubation. For comparison purpose, the minimum inhibitory concentrations of amikacin were also determined in the same manner as stated above.

The antibacterial spectra of these new compounds of this invention and of the known, comparative compound are shown in Table 1 below.

value of more than 100 mg/kg when their acute toxicity is estimated by intravenous injection in mice.

The new compounds of this invention are usually obtained in the form of its free base or a hydrate or a carbonate thereof. The new compounds of this invention each may readily be converted into a form of a pharmaceutically acceptable acid addition salt thereof, such as the hydrochloride, hydrobromide, sulfate, phosphate, nitrate, acetate, maleate, citrate, ascorbate, methanesulfonate and the like by reacting with the appropri-

TABLE 1

| Test organisms | MIC. (mcg/ml) | | |
| --- | --- | --- | --- |
| | Hexadeoxy-kanamycin | Hexadeoxy-amikacin | Amikacin (Comparative) |
| *Staphylococcus aureus* FDA 209P | 1.56 | 0.78 | 0.78 |
| *Staphylococcus aureus* Smith | 0.78 | 1.56 | 0.39 |
| *Staphylococcus aureus* Ap01 | 3.13 | 3.13 | 1.56 |
| *Staphylococcus epidermidis* 109 | 3.13 | 1.56 | 3.13 |
| *Micrococcus flavus* FDA 16 | 12.5 | 6.25 | 6.25 |
| *Micrococcus luteus* PCI 1001 | 12.5 | 6.25 | 3.13 |
| *Bacillus anthracis* | 1.56 | 1.56 | 0.78 |
| *Bacillus subtilis* PCI 219 | 0.78 | 0.78 | 0.39 |
| *Bacillus subtilis* NRRL B-558 | 0.78 | 0.78 | 0.39 |
| *Bacillus cereus* ATCC 10702 | 6.25 | 6.25 | 6.25 |
| *Corynebacterium bovis* 1810 | 6.25 | 6.25 | 1.56 |
| *Mycobacterium smegmatis* ATCC 607 | 0.78 | 1.56 | 0.78 |
| *Escherichia coli* NIHJ | 3.13 | 1.56 | 1.56 |
| *Escherichia coli* K-12 | 1.56 | 0.78 | 0.39 |
| *Escherichia coli* K-12 R5 | >100 | 100 | 100 |
| *Escherichia coli* K-12 R 388 | 1.56 | 0.78 | 0.39 |
| *Escherichia coli* K-12 J5R 11-2 | 25 | 1.56 | 1.56 |
| *Escherichia coli* K-12 ML 1629 | 25 | 1.56 | 1.56 |
| *Escherichia coli* K-12 ML 1630 | 25 | 3.13 | 3.13 |
| *Escherichia coli* K-12 ML 1410 | 3.13 | 3.13 | 1.56 |
| *Escherichia coli* K-12 ML 1410 R81 | 25 | 3.13 | 1.56 |
| *Escherichia coli* K-12 LA 290 R55 | 100 | 1.56 | 1.56 |
| *Escherichia coli* K-12 LA 290 R56 | 12.5 | 1.56 | 0.78 |
| *Escherichia coli* K-12 LA 290 R64 | 25 | 3.13 | 1.56 |
| *Escherichia coli* W677 | 1.56 | 0.78 | 0.78 |
| *Escherichia coli* JR66/W677 | >100 | 3.13 | 3.13 |
| *Escherichia coli* K-12 C 600R135 | 1.56 | 1.56 | 0.78 |
| *Escherichia coli* JR255 | 1.56 | 0.78 | 0.78 |
| *Klebsiella pneumoniae* PCI 602 | 1.56 | 1.56 | 0.78 |
| *Klebsiella pneumoniae* 22 #3038 | >100 | 3.13 | 3.13 |
| *Shigella dysenteriae* JS 11910 | 6.25 | 6.25 | 3.13 |
| *Shigella flexneri* 4b JS11811 | 6.25 | 6.25 | 3.13 |
| *Shigella sonnei* JS11746 | 3.13 | 3.13 | 3.13 |
| *Salmonella typhi* T-63 | 0.78 | 0.78 | 0.39 |
| *Salmonella enteritidis* 1891 | 1.56 | 3.13 | 1.56 |
| *Proteus vulgaris* OX19 | 1.56 | 0.78 | 1.56 |
| *Proteus rettgeri* GN311 | 0.78 | 1.56 | 0.39 |
| *Proteus rettgeri* GN466 | 1.56 | 1.56 | 0.78 |
| *Serratia marcescens* | 6.25 | 6.25 | 1.56 |
| Serratia SOU | >100 | 50 | 25 |
| Serratia 4 | 25 | 12.5 | 3.13 |
| Providencia Pv 16 | 12.5 | 3.13 | 1.56 |
| Providencia 2991 | 50 | 6.25 | 1.56 |
| *Pseudomonas aeruginosa* A3 | 3.13 | 0.78 | <0.20 |
| *Pseudomonas aeruginosa* No. 12 | 50 | 25 | 3.13 |
| *Pseudomonas aeruginosa* H9 | 100 | 50 | 6.25 |
| *Pseudomonas aeruginosa* Hi1 | >100 | 100 | 12.5 |
| *Pseudomonas aeruginosa* TI-13 | 50 | 12.5 | 3.13 |
| *Pseudomonas aeruginosa* GN315 | >100 | >100 | 25 |
| *Pseudomonas aeruginosa* 99 | >100 | 50 | 6.25 |
| *Pseudomonas aeruginosa* B-13 | >100 | 50 | 6.25 |
| *Pseudomonas aeruginosa* 21-75 | >100 | 100 | 12.5 |
| *Pseudomonas aeruginosa* PST1 | >100 | 50 | 12.5 |
| *Pseudomonas aeruginosa* ROS134/PU21 | >100 | >100 | 100 |
| *Pseudomonas aeruginosa* K-Ps102 | >100 | 50 | 6.25 |
| *Pseudomonas maltophilia* GN907 | >100 | >100 | >100 |

From Table 1, it is seen that the new compounds of this invention according to the general formula (I) effectively inhibit the growth of many kinds of bacterial strains. The new compounds of this invention show a low acute toxicity to animal, as it has been found that the new compounds of this invention exhibit an $LD_{50}$ ate, pharmaceutically acceptable inorganic or organic acid in an aqueous medium.

The new compounds of the formula (I) according to this invention and its pharmaceutically acceptable acid addition salt may be administered orally, intraperitoneally, intravenously, subcutaneously or intramuscularly using any pharmaceutical form known to the art for such administration and in a similar manner to the known kanamycins. For instance, the new compounds of this invention may be administered orally using any pharmaceutical form known to the art for oral administration. Examples of the pharmaceutical forms for oral administration are powders, capsules, tablets, syrup and the like. A suitable dose of the new compounds of this invention for effective treatment of bacterial infections is in a range of 0.2 to 2 g. per person a day when it is given orally. It is preferred that said dose should be orally administered in three to four aliquots per day. The new compounds of this invention may also be administered by intramuscular injection at a dosage of 100 to 1000 mg per person two to four times per day. Moreover, the new compounds of this invention may be formulated into an ointment for external application which contains the active compound at a concentration of 0.5~5% by weight in mixture with a known ointment base such as polyethylene glycol. Furthermore, the new compounds of this invention are each useful for sterilization of surgical instruments and sanitary materials.

According to a second aspect of this invention, therefore, there is provided an antibacterial composition comprising as the active ingredient 5,2',3',4',4'',6''-hexadeoxykanamycin or 1-N-[(S)-4-amino-2-hydroxybutyryl]-5,2',3',4',4'',6''-hexadeoxykanamycin as defined by the formula (I) or a pharmaceutically acceptable acid-addition salt thereof in an antibacterially effective amount to inhibit the growth of bacteria, in combination with a carrier for the active ingredient compound.

Next, the production of the new compounds of this invention according to the general formula (I) is described.

Thus, the hexadeoxykanamycin, that is, one of the new compounds of this invention can be synthesized starting from 3',4'-dideoxykanamycin which was semisynthetically prepared by the present inventors (see Japanese patent application No. 11402/79; Japanese patent application prepublication "Kokai" No. 105699/80; U.S. Pat. No. 4,298,727).

According to a third aspect of this invention, there is provided a process for the production of 5,2',3',4',4'',6''-hexadeoxykanamycin as defined by the formula (I), which comprises the consecutive steps of:

(a) converting 3',4'-dideoxykanamycin into a tetra-N-protected derivative of 3',4'-dideoxykanamycin represented by the general formula (II)

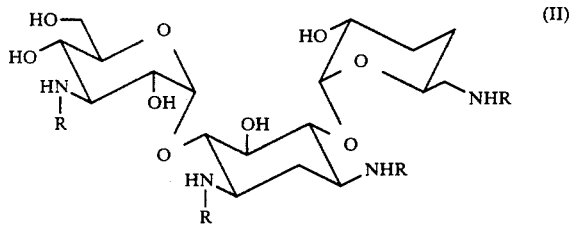

wherein R denotes an alkyloxycarbonyl group, a cycloalkyloxycarbonyl group or an aralkyloxycarbonyl group as an amino-protecting group of the formula

where B is an alkyl group of 1 to 4 carbon atoms, a cycloalkyl group of 3 to 6 carbon atoms or an aralkyl group, particularly benzyl group, (b) reacting the tetra-N-protected 3',4'-dideoxykanamycin derivative of the formula (II) with a basic reagent in an anhydrous organic solvent to produce a cyclic 2'',3''-carbamate derivative represented by the formula (III)

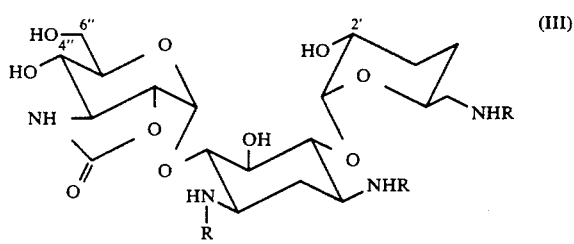

wherein R is the amino-protecting group as defined above, (c) reacting the cyclic 2'',3''-carbamate derivative of the formula (III) with trifluoromethanesulfonyl chloride to sulfonylate the 2'-, 4''- and 6''-hydroxyl groups of the cyclic 2'',3''-carbamate compound of the formula (III) and thereby produce the compound of the formula (IV)

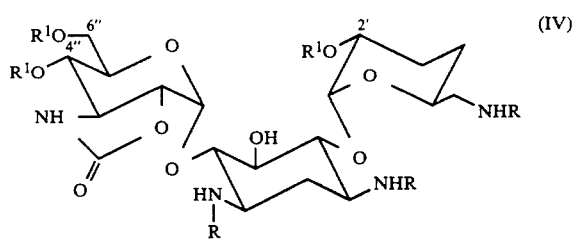

wherein R is the amino-protecting group as defined above and $R^1$ denotes a trifluoromethanesulfonyl group $-SO_2CF_3$, (d) reacting the compound of the formula (IV) with sodium thiophenolate to replace the 2'-, 4''- and 6''-trifluoromethanesulfonyloxy groups ($R^1O-$) of the compound of the formula (IV) each by a phenylthio group and thereby produce the compound of the formula (V)

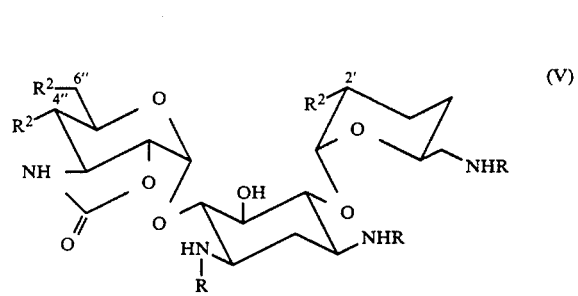

wherein R is the amino-protecting group as defined above and $R^2$ denotes a phenylthio group $-SC_6H_5$, (e) subjecting the compound of the formula (V) to hydrogenolysis to replace the 2'-, 4''- and 6''-phenylthio groups ($R^2$) each by a hydrogen atom and thereby produce the compound of the formula (VI)

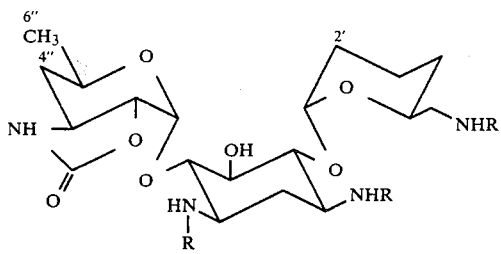

(VI)

wherein R is the amino-protecting group as defined above, (f) reacting the compound of the formula (VI) with carbon disulfide, sodium hydroxide and methyl iodide to convert the 5-hydroxyl group of said compound (VI) into an S-methyldithiocarbonyloxy group and thereby produce a compound of the formula (VII)

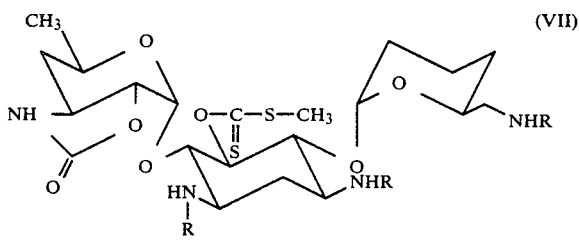

(VII)

wherein R is the amino-protecting group as defined above, (g) subjecting the 5-S-methyldithiocarbonylated compound of the formula (VII) to hydrogenolysis to remove the 5-S-methyldithiocarbonyloxy group from the compound (VII) and thereby produce the 5-deoxygenated compound of the formula (VIII)

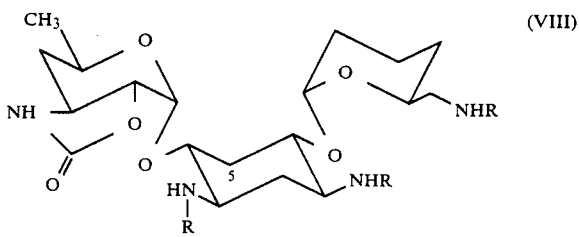

(VIII)

wherein R is the amino-protecting group as defined above, (h) hydrolyzing the 5-deoxygenated compound of the formula (VIII) under alkaline conditions to fission the cyclic 2″,3″-carbamate ring of said compound and thereby produce the compound of the formula (IX)

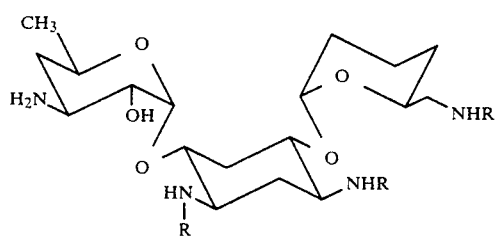

(IX)

wherein R is the amino-protecting group as defined above, and (i) removing the amino-protecting groups (R) from the compound of the formula (IX) in a known manner to produce the 5,2′,3′,4′,4″,6″-hexadeoxykanamycin of the formula (Ia)

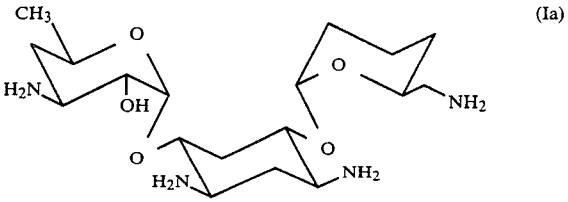

(Ia)

The process of the third aspect of this invention may include a further step of converting the hexadeoxykanamycin (Ia) into a pharmaceutically acceptable acid-addition salt thereof by reacting with a pharmaceutically acceptable inorganic or organic acid in a known manner, if desired.

The procedures for working out the process of the third aspect of this invention are now described in detail.

In the step (a) of the present process, the conversion of the starting 3′,4′-dideoxykanamycin into its tetra-N-protected derivative is carried out by reacting the four 1-, 3-, 6′- and 3″-amino groups of the 3′,4′-dideoxykanamycin each with a known reagent for introduction of an amino-protecting group of the formula

where B is an alkyl group of 1~4 carbon atoms, a cycloalkyl group of 3 to 6 carbon atoms or an aralkyl group, particularly benzyl group. The introduction of the amino-protecting group (R) into the four amino groups of the starting 3′,4′-dideoxykanamycin may be achieved by means of a known amino-protecting technique previously adopted in the semisynthesis of some known deoxy derivative of kanamycins, as described, for example, in U.S. Pat. Nos. 3,781,268; 3,929,762; and 3,939,143 or U.K. patent No. 1,426,908. Suitable examples of the amino-protecting group (R) to be introduced into the starting 3′,4′-dideoxykanamycin are of the urethane-type amino-protecting group, including an alkyloxycarbonyl group such as tert-butoxycarbonyl and tert-amyloxycarbonyl; a cycloalkyloxycarbonyl group such as cyclohexyloxycarbonyl; and an aralkyloxycarbonyl group such as benzyloxycarbonyl. The introduction of the amino-protecting group of these kinds may be conducted by reacting the starting B 3′,4′-dideoxykanamycin with an appropriate known reagent for introduction of the amino-protecting group which may be in the form of an acid halide, acid azide, active ester or acid anhydride and the like, in the manner known in the conventional synthesis of peptides.

In the step (b) of the present process, the tetra-N-protected 3′,4′-dideoxykanamycin derivative (II) may be dissolved in an appropriate inert organic solvent such as N,N-dimethylformamide and then reacted with the basic reagent such as an alkali metal hydride, especially sodium hydride at ambient temperature, similarly to a known method as described in the "Journal of Antibiotics" Vol. 25, No. 12, 741~742 (1972) or U.S. Pat. No. 4,125,706. This step (b) should be effected under anhydrous conditions, and in this step (b) there occurs a condensation reaction where the 2″-hydroxyl group is condensed with the urethane-type N-protected 3″-amino group to form the 2″,3″-carbamate ring and afford the 1,3,6′-tris-N-protected 3′,4′-dideoxykanamycin 2″,3″-carbamate according to the general formula (III) given hereinbefore.

In the step (c) of the present process, the 2″,3″-carbamate derivative (III) is reacted with 3 molar proportion or a slight excess of trifluoromethanesulfonyl chloride (CF$_3$SO$_2$Cl) in dry pyridine at a temperature of 0° C. to 30° C. for a time of 20 minutes to 3 hours to give the 2′,4″,6″-tris-O-trifluoromethanesulfonylated derivative of the general formula (IV). In place of trifluoromethanesulfonyl chloride, there may be employed trifluoromethanesulfonic acid anhydride, if desired.

In the step (d) of the present process, the trifluoromethanesulfonylated compound (IV) is reacted with 3 molar proportions or more of sodium thiophenolate (C$_6$H$_5$SNa) in dry N,N-dimethylformamide (DMF) or other suitable organic solvent such as dioxane, acetone or tetrahydrofuran (TMF) at a temperature of 10° C. to 40° C., preferably at ambient temperature for a time of 1 to 5 hours to effect the thiophenylation at the 2′-, 4″- and 6″-positions of the compound (IV) and thereby produce the 2′,4″,6″-trithiophenylated compound of the formula (V).

In the step (e) of the present process, the thiophenylated compound (V) is subjected to hydrogenolysis to remove the 1-, 4″- and 6″-phenylthio groups therefrom, that is to say, to replace these three phenylthio groups each by a hydrogen atom. To this end, the thiophenylated compound (V) is reacted with Ranney nickel in ethanol under refluxing to afford the 1,3,6′-tri-N-protected 2′,3′,4′,4″,6″-pentadeoxykanamycin 2″,3″-carbamate of the general formula (VI).

In the steps (f) and (g) of the present process, the less reactive 5-hydroxyl group of the N-protected 2′,3′,4′,4″,6″-pentadeoxykanamycin compound of the formula (VI) should be removed to effect the 5-deoxygenation. For this purpose, the step (f) is carried out where the compound (VI) is at first reacted with an excess amount of carbon disulfide in an appropriate inert organic solvent such as dimethylsulfoxide in the presence of aqueous sodium hydroxide under ice-cooling, followed by reacting with an excess amount of methyl iodide at ambient temperature to effect S-methyldithiocarbonylation at the 5-position of the kanamycin compound (VI) and thereby to produce the 5-S-methyldithiocarbonylated compound of the formula (VII). In the subsequent step (g) of the present process, the 5-S-methyldithiocarbonylated compound (VII) is subjected to hydrogenolysis to remove the 5-S-methyldithiocarbonyloxy group therefrom. For this purpose, it is convenient to effect the hydrogenolysis by reacting the compound (VII) with tributylstannane in dry toluene in the presence of α,α′-azobisisobutyronitrile at an elevated temperature under an inert atmosphere such as argon gas. In this way, there is afforded the 1,3,6′-tri-N-protected 5,2′,3′,4′,4″,6″-hexadeoxykanamycin 2″,3″-carbamate compound of the formula (VIII).

In the further steps (h) and (i) of the present process, the N-protecting groups remaining in the N-protected 5,2′,3′,4′,4″,6″-hexadeoxykanamycin compound of the formula (VIII) are removed therefrom. To this end, the compound (VIII) is hydrolyzed in the step (h) under alkaline conditions in an aqueous organic solvent such as aqueous dioxane containing an amount of alkali metal carbonate such as sodium carbonate or barium hydroxide to fission the 2″,3″-carbamate ring of the compound (VIII). The hydrolysis may be effected at a temperature of 20° to 100° C. in the same manner as described in U.S. Pat. No. 4,125,706, and the hydrolytic fission of the 2″,3″-carbamate ring liberates the free 2″-hydroxyl group and free 3″-amino group, affording the 1,3,6′-tri-N-protected 5,2′,3′,4′,4″,6″-hexadeoxykanamycin compound of the formula (IX). In the subsequent step (i) of the present process, the three amino-protecting groups (R) remaining in the compound (IX) are removed in a known manner according to the conventional deprotecting technique which is known in the synthesis of peptides, for instance, by catalytic hydrogenolysis, depending on the nature of the remaining amino-protecting groups (R). Thus, the amino-protecting group of the alkyloxycarbonyl type or the cycloalkyloxycarbonyl type may be removed either by alkaline hydrolysis, preferably by heating in a saturated solution of barium hydroxide in water, aqueous 5N sodium hydroxide or aqueous 5N potassium hydroxide; or by acidic hydrolysis, preferably by treating with an acid, for example, 1N hydrochloric acid in aqueous methanol or aqueous trifluoroacetic acid at ambient temperature or at an elevated temperature. The amino-protecting group of the aralkyloxycarbonyl type such as benzyloxycarbonyl may be removed by hydrogenolysis which is effected in water or in aqueous or anhydrous organic solvent such as dioxane, methanol and the like at ambient temperature or at an elevated temperature in the presence of a known hydrogenolysis catalyst such as palladium-carbon using hydrogen gas under atmospheric, superatmospheric or subatmospheric pressure. The reaction mixture from the N-deprotection reaction may be neutralized, if desired, before the desired hexadeoxykanamycin of the formula (Ia) is recovered therefrom. The desired hexadeoxykanamycin compound of the formula (Ia) may be isolated and purified chromatographically in the same manner as in the conventional technique of purifying the known water-soluble, basic antibiotics with aid of ion-exchange resins. For instance, the reaction solution containing the desired hexadeoxykanamycin (Ia) dissolved therein may be treated with a cation-exchange resin such as Amberlite IRC-50 or Amberlite CG-50 (both are the products of Rohm & Haas Co., U.S.A.) for adsorption of the active compound and the resin may then be eluted with aqueous ammonia at different concentrations, followed either by concentration of the active fractions of the eluate to dryness, or by dry-freezing of the active fractions of the eluate. In this way, the desired new compound (Ia) of this invention is obtained and if desired, it may be converted into an acid-addition salt by reacting with a pharmaceutically acceptable acid in a known manner.

According to a fourth aspect of this invention, there is provided a process for the production of 1-N-[(S)-4-amino-2-hydroxybutyryl]-5,2′,3′,4′,4″,6″-hexadeoxykanamycin represented by the formula (Ib)

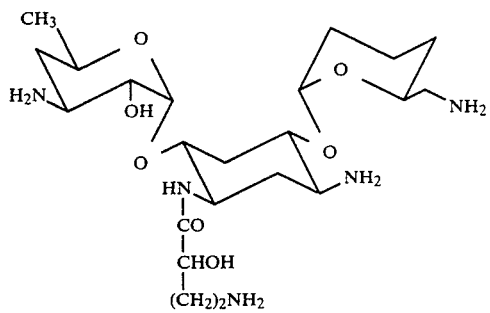

which comprises the steps of:

(i) acylating the 1-amino group of 5,2′,3′,4′,4″,6″-hexadeoxykanamycin or its partially N-protected derivative represented by the formula (Ic)

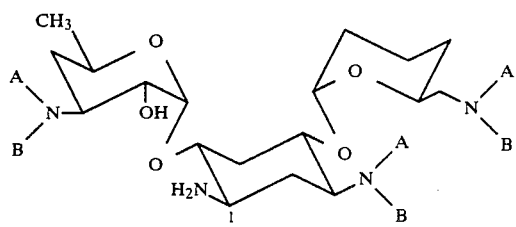

wherein A is a hydrogen atom and B is a hydrogen atom, or A is a hydrogen atom and at least one B is a monovalent amino-protecting group but the other B(s) is or are each a hydrogen atom, or at least one pair of A and B taken together form a di-valent amino-protecting group but the other A and B are each a hydrogen atom, by reacting with (S)-4-amino-2-hydroxybutyric acid or an amino-protected derivative thereof represented by the formula (X)

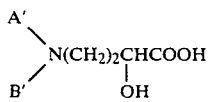

wherein A′ is a hydrogen atom and B′ is a hydrogen atom or a mono-valent amino-protecting group, or A′ and B′ taken together from a di-valent amino-protecting group, or a functional equivalent of the compound (X), to produce the 1-N-acylated product represented by the formula (XI)

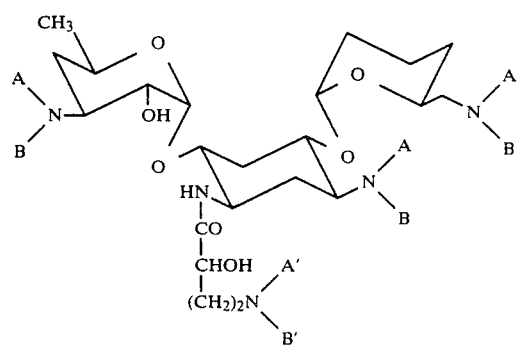

wherein A, B, A′ and B′ are as defined above, and (ii) removing the remaining amino-protecting groups, where exist, from the 1-N-acylated product of the formula (XI) in a known manner to produce the desired compound of the formula (Ib).

The procedures for working out the process of the fourth aspect of this invention are now described in detail.

In carrying out the present process, it is possible to employ as the starting compound 5,2′,3′,4′,4″,6″-hexadeoxykanamycin of the formula (Ia) of which all the amino groups are not protected, in the form of the free base or in the form of an acid-addition salt such as hydrochloride or sulfate. However, it is preferred to employ as the starting compound such a partially amino-protected derivative of the hexadeoxykanamycin (Ia) in which all or some of the amino groups other than the 1-amino group have been protected with known amino-protecting groups and which may be prepared by introduction of a known amino-protecting group into the hexadeoxykanamycin (Ia) by means of a known amino-protecting techniques previously employed in the semi-synthesis of known deoxykanamycin derivatives. For the preparation of the partially amino-protected 5,2′,3′,4′,4″,6″-hexadeoxykanamycin derivative of the formula (Ic), it is feasible to utilize the amino-protecting techniques which were employed, for instance, in the preparation of the 6′-N-benzyloxycarbonyl derivative of kanamycin B as described in the specification of U.S. Pat. No. 3,781,268 or U.S. Pat. No. 3,929,762; or the preparation of 2′,6′-di-N-tert-butoxycarbonylkanamycin B or 6′-N-benzyloxycarbonyl-kanamycin B, or the mono-N- or di-N-tert-butoxycarbonyl and even tri-N-tert-butoxycarbonyl derivative of 6′-N-benzyloxycarbonylkanamycin B, either isolated or in mixture thereof, as described in the specification of U.K. Pat. No. 1,426,908 or U.S. Pat. No. 3,939,143.

In general, suitable examples of the amino-protecting group which may be used for the protection of some amino groups in the partially amino-protected derivative of the formula (Ic) may be an ordinary amino-protecting group, and tert-amyloxycarbonyl; a cycloalkyloxycarbonyl group such as cyclohexyloxycarbonyl; an aralkyloxycarbonyl group such as benzyloxycarbonyl; an acyl group such as trifluoroacetyl and o-nitrophenoxyacetyl; a phosphinothioyl group such as diphenylphosphinothioyl and dimethylphosphinothioyl; a phosphinyl group such as diphenylphosphinyl, and the like. Preferred examples of the di-valent amino-protecting group include phthaloyl group and a group of Schiff base type such as salicylidene. The introduction of the amino-protecting group of these kinds may be conducted by reacting the compound of the formula (Ia) with an appropriate known reagent for introduction of the amino-protecting group which may be in the form of an acid halide, acid azide, active ester or acid anhydride and the like, in the manner known in the conventional synthesis of peptides. By chosing the quantity of the reagent for introduction of the amino-protecting group employed in a proportion of 0.5 to 6 mol. per mol. of the compound of the formula (Ia), it is possible to prepare a mixture of different, partially amino-protected derivatives (Ic) at any ratio, due to the difference in the reactivity of the respective amino groups of the compound (Ia).

In the process of the fourth aspect of this invention, it is practical to employ as the starting compound such N-protected hexadeoxykanamycin derivative in which all or some of the amino groups other than the 1-amino group have or has been blocked, for example, a 3,6′,3″- tri-N-protected derivative, a 3,6′-di-N-protected derivative, a 6′,3″-di-N-protected derivative and a 6′-mono-N-protected derivative. Besides, a mixture of two or more of these partially N-protected derivatives may, without being purified, be used for the 1-N-acylation step of the present process.

In order to ensure that the desired 1-N-acylated product of the general formula (Ib) can be produced in a high yield in accordance with the process of the fourth aspect invention, it needs only that just the 1-amino group of the compound of the formula (Ia), namely the hexadeoxykanamycin is selectively acylated with the (S)-4-amino-2-hydroxybutyric acid (X). Accordingly, it will be evident that most preferably, a 3,6′,3″-tri-N-protected derivative of the compound (Ia), that is, the N-protected derivative of the compound (Ia) in which all the amino groups other than the 1-amino group have been blocked with the protective groups is employed as the starting compound to be 1-N-acylated in the present process.

To prepare the 3,6′,3″-tri-N-protected derivative of the formula (Ic) from the compound of the formula (Ia), the following procedure may be used, for instance. Thus, there can be applied a known method of claim 1 of U.S. Pat. No. 4,297,485 (corresponding to our pending Japanese patent application No. 138402/78) by which a 3,6′,3″-tri-N-acylated protected derivative of kanamycin A is prepared by reacting kanamycin A with zinc cation for the formation of a metal complex of kanamycin A, reacting this kanamycin A-metal complex with an acylation agent known as the amino-protecting group-introducing reagent for the protection of all the amino groups other than the 1-amino group of the kanamycin A moiety of the kanamycin A-metal complex [said 1-amino group only having been blocked by complexing with the di-valent zinc cation in the kanamycin A-metal complex, because of lacking the 4″-hydroxyl group in the compound of the formula (Ia)], and then removing the zinc cation from said complex, eg., by dilution with ethyl ether or by treatment with aqueous ammonia. In this way, a 3,6′,3″-tri-N-protected derivative of the formula (Ic) can be prepared from the compound of the formula (Ia) in a high yield.

In the process of this fourth aspect invention, the 1-amino group of the compound of the formula (Ic), either isolated or in mixture of two or more of them, is acylated with the (S)-4-amino-2-hydroxybutyric acid of the formula (X) of which the amino group is not protected or has been protected.

In the process of the fourth aspect invention, the 1-N-acylation with the (S)-4-amino-2-hydroxybutyric acid (X) may be conducted according to any of one conventional methods for the synthesis of peptides, for instance, according to the known dicyclohexylcarbodiimide method, the known mixed acid anhydride method, the known azide method or the active ester method and the like, using the (S)-4-amino-2-hydroxybutyric acid (X) as such or in the form of its reactive derivative (as the functional equivalent thereof). For the amino-protecting group for protection of the amino group of the α-hydroxy-ω-aminoalkanoic acid (X) may be employed such as amino-protecting group which is the same as or different from the one present in the starting compound (Ic). Benzyloxycarbonyl group which is removable by conventional hydrogenolysis in the presence of a catalyst such as palladium or platinum oxide is a convenient N-protecting group.

The 1-N-acylation in the present process may preferably be carried out in an aqueous organic solvent according to the active ester method using the (S)-4-amino-2-hydroxybutyric acid (X) in the form of its active ester. For example, N-hydroxysuccinimide ester of (S)-4-benzyloxycarbonylamino-2-hydroxybutyric acid may preferably be used as the active ester which may be prepared by a conventional method of preparing the active ester. This active ester preferably may be used in a proportion of from 0.5 to 3 molar equivalents and preferably of from 1 to 1.5 molar equivalents per mol of the starting compound (Ic) to be 1-N-acylated. The aqueous organic solvent used in the reaction medium may be a water-miscible organic solvent such as dioxane, 1,2-dimethoxyethane, N,N-dimethylformamide, tetrahydrofuran, and the like. The 1-N-acylation may be effected at ambient temperature or, if desired, at an elevated temperature of 20°~90° C. and for a reaction time of several hours and preferably of 5~6 hours.

In the second step of the process of this fourth aspect invention, the 1-N-acylation product (including the mixed acylation products) as obtained in the 1-N-acylation step of the present process is subjected to the de-protecting reaction, ie., the removal of the amino-protecting groups, if these are still remaining in the 1-N-acylation product. The removal of the protecting groups is effected by a conventional deprotecting technique. Thus, the amino-protecting group of the alkyloxycarbonyl type is removed by weak acid hydrolysis with an aqueous solution of trifluoroacetic acid or acetic acid and the like or with a diluted aqueous solution of an inorganic acid such as hydrochloric acid. The aralkyloxycarbonyl group such as benzyloxycarbonyl may be removed by an ordinary catalytic reduction (hydrogenolysis). When phthaloyl group is present as the amino-protecting group, it can be removed by heating in a solution of hydrazine hydrate in a lower alkanol.

The N-deprotected acylation product as obtained from the second, de-protecting step of the present process may contain the desired 1-N-acylation product of the formula (Ib). The desired 1-N-[(S)-4-amino-2-hydroxybutyl]-hexadeoxykanamycin (Ib) may be isolated and purified chromatographically using a cation-exchanger containing carboxylic functions, such as Amberlite CG-50 (a product of Rohm & Haas Co., U.S.A.) or CM-Sephadex C-25 (a product of Pharmacia Co., Sweden) and assaying the antibacterial activity of the fractions of the eluate by means of a proper kanamycin-sensitive strain and kanamycin-resistant strain of bacteria.

This invention is now illustrated with reference to the following Examples to which this invention is not limited.

EXAMPLE 1

Synthesis of 5,2′,3′,4′,4″,6″-hexadeoxykanamycin (a) 3′,4′-Dideoxykanamycin (1.20 g; 2.65 milimoles) was admixed with 20 ml of water, 20 ml of methanol and 17 ml (12.2 milimoles) of triethylamine until the dissolution took place. The resultant solution of 3′,4′-dideoxykanamycin was then mixed with a solution of 5.03 g (18.4 milimoles) of benzyl S-4,6-dimethylpyrimid-2-ylthiocarbonate in 20 ml of methanol, followed by stirring at ambient temperature for 24 hours to effect the amino-protecting reaction for introduction of the benzyloxycarbonyl groups into the four amino groups of the starting 3′,4′-dideoxykanamycin. The reaction solution was then admixed with 0.5 ml of 17% aqueous ammonia and concentrated to dryness under reduced pressure. The residue so obtained was washed twice with 30 ml portions of water and once with 30 ml of n-hexane to give 2.30 g of a colorless powder comprising 1,3,6',3''-tetrakis(N-benzyloxycarbonyl)-3',4'-dideoxykanamycin. Yield 79%.

(b) 1,3,6',3''-Tetrakis(N-benzyloxycarbonyl)3',4'-dideoxykanamycin (2.20 g; 2.01 milimoles) obtained in the above step (a) was dissolved in 20 ml of anhydrous N,N-dimethylformamide, and to the resultant solution was added 804 mg (20.1 milimoles) of sodium hydride (as a suspension of 60% sodium hydride in oil), followed by stirring at ambient temperature for 3 hours (for the formation of the cyclic 2'',3''-carbamate derivative). The resulting reaction solution was admixed with 1.2 ml (20.1 milimoles) of acetic acid and concentrated to dryness. The residue obtained was washed with 200 ml of water to afford 1.10 g of a colorless powder comprising 1,3,6'-tris(N-benzyloxycarbonyl)-3',4'-dideoxykanamycin 2'',3''-carbamate. Yield 62%. This 2'',3''-carbamate compound showed a decomposition temperature of 221°~226° C. $[\alpha]_D^{23} + 67°$ (c 1, N,N-dimethylformamide).

Elemental analysis: Found: C 58.84%, H 5.63%, N 6.31%. Calcd. for $C_{43}H_{52}N_4O_{16}$: C 58.63%, H 5.95%, N 6.36%.

(c) 1,3,6'-Tris(N-benzyloxycarbonyl)-3',4'-dideoxykanamycin 2'',3''-carbamate (1.05 g) obtained in the above step (b) was dissolved in 80 ml of dry pyridine, and the resultant solution was admixed with 436 mg (3.57 milimoles) of 4-dimethylaminopyridine, followed by dropwise addition thereto of 1.14 ml (10.2 millimoles) of trifluoromethanesulfonyl chloride under ice-cooling and further by agitation of the resultant admixture at ambient temperature for 2 hours (for the trifluoromethanesulfonylation of the 2'-, 4''- and 6''-hydroxyl groups of the 3',4'-dideoxykanamycin compound). The reaction solution obtained was admixed with 1 ml of water and concentrated, and the residue was dissolved in 50 ml of ethyl acetate to give the solution which was then washed with 50 ml of a saturated aqueous sodium hydrogen carbonate and then with 50 ml of water. The solution in ethyl acetate so washed was dried over anhydrous sodium sulfate and then concentrated to dryness. The residue obtained was purified by column chromatography on silica gel (100 g, Wako Gel C-200, a product of Wako Junyaku Co., Japan) developed with chloroform-methanol (60:1) with collecting the eluate in 20 ml-fractions. The fractions Nos. 47~61 were combined together and concentrated to dryness to give 623 mg of 1,3,6'-tris(N-benzyloxycarbonyl)-2',4'',6''-tris(O-trifluoromethanesulfonyl)-3',4'-dideoxykanamycin 2,3''-carbamate. Yield 41%.

(d) 1,3,6'-Tris(N-benzyloxycarbonyl)-2',4'',6''-tris(O-trifluoromethanesulfonyl)-3',4'-dideoxykanamycin 2'',3''-carbamate (620 mg; 0.485 milimoles) obtained in the above step (c) was dissolved in 70 ml of anhydrous N,N-dimethylformamide, and to the resultant solution was added 385 mg (2.91 milimoles) of sodium thiophenolate ($C_6H_5SNa$), followed by agitation at ambient temperature for 2 hours (for the thiophenylation). The reaction solution was concentrated to dryness and the residue was taken up into 30 ml of ethyl acetate. The solution obtained was washed twice with 30 ml portions of water, the ethyl acetate phase was dried over anhydrous sodium sulfate and then concentrated to dryness. The residue was purified by column chromatography on silica gel (Wako Gel C-200, 70 g) developed with chloroform-methanol (60:1) with collecting the eluate in 14 ml-fractions. The fractions Nos. 36~53 were combined together and concentrated to dryness to afford 415 mg of 1,3,6'-tris(N-benzyloxycarbonyl)-2',4'',6''-triphenylthio-2',3',4',4'',6''-pentadeoxykanamycin 2'',3''-carbamate. Yield 74%.

(e) 1,3,6'-Tris(N-benzyloxycarbonyl)-2',4'',6''-triphenylthio-2',3',4',4'',6''-pentadeoxykanamycin 2'',3''-carbamate (411 mg; 0.355 milimoles) obtained in the above step (d) was dissolved in 50 ml of ethanol. The solution obtained was admixed with 500 mg of Ranney nickel (R-200, a product of Nikko Rikagaku Sangyo Co., Japan), followed by refluxing at 90° C. for 2 hours to effect the hydrogenolysis for the removal of the 2'-, 4''- and 6''-phenylthio groups. The reaction mixture was filtered to remove the Ranney nickel catalyst, and the filtrate was concentrated to dryness. The residue was purified by column chromatography on silica gel (Wako Gel C-200, 50 g) developed with chloroform-methanol (50:1) with collecting the eluate in 10 ml-fractions. The fractions Nos. 53~76 were combined together and concentrated to dryness to afford 213 mg of 1,3,6'-tris(N-benzyloxycarbonyl)-2',3',4',4'',6''-pentadeoxykanamycin 2'',3''-carbamate. Yield 72%.

(f) 1,3,6'-Tris(N-benzyloxycarbonyl)-2',3',4',4'',6''-pentadeoxykanamycin 2'',3''-carbamate (209 mg; 0.251 milimoles) obtained in the above step (e) was dissolved in 2 ml of dimethylsulfoxide. To the resultant solution was added 0.15 ml (2.51 milimoles) of carbon disulfide and further dropwise added 0.25 ml of 5N aqueous sodium hydroxide (1.25 milimoles) under ice-cooling, followed by agitation for 30 minutes under ice-cooling. To the reaction solution obtained was added 0.16 ml (2.51 milimoles) of methyl iodide, followed by agitation at ambient temperature for 2 hours to effect the S-methyldithiocarbonylation of the 5-hydroxyl group. The reaction mixture was then mixed with 20 ml of water and extracted twice with 20 ml portions of ethyl acetate. The extract in ethyl acetate was dried over anhydrous sodium sulfate and concentrated to dryness. The residue was purified by column chromatography on silica gel (Wako Gel C-200, 20 g) developed with chloroform-methanol (80:1) with collecting the eluate in 4 ml-fractions. The fractions Nos. 47~62 were combined together and concentrated to dryness to give 165 mg of 1,3,6'-tris(N-benzyloxycarbonyl)-2',3',4',4'',6''-pentadeoxy-5-O-(S-methyldithiocarbonyl)kanamycin 2'',3''-carbamate. Yield 71%.

(g) 1,3,6'-Tris(N-benzyloxycarbonyl)-2',3',4',4'',6''-pentadeoxy-5-O-(S-methyldithiocarbonyl)kanamycin 2'',3''-carbamate (162 mg; 0.176 milimoles) obtained in the above step (f) was dissolved in 5 ml of dry toluene, and to the resulting solution were added 5 mg of $\alpha,\alpha'$-azobisisobutyronitrile and 1 ml of tributylstannane, followed by stirring at 80° C. under atmosphere of argon gas to effect the hydrogenolysis (for removal of the 5-S-methyldithiocarbonyloxy group). The reaction solution was concentrated to dryness and the residue was purified by column chromatography on silica gel (Wako Gel C-200, 20 g) developed with chloroform-methanol (50:1) with collecting the eluate in 4 ml-fractions. The fractions Nos. 37~49 were combined together and concentrated to dryness to afford 112 mg of 1,3,6'-tris(N-benzyloxycarbonyl)-5,2',3',4',4'',6''-hexadeoxykanamycin 2'',3''-carbamate. Yield 78%.

(h) 1,3,6'-Tris(N-benzyloxycarbonyl)-5,2',3',4',4'',6''-hexadeoxykanamycin 2'',3''-carbamate (108 mg; 0.132 milimoles) obtained in the above step (g) was dissolved in 5 ml of dioxane, and the resultant solution was admixed with 6 ml of 0.1N aqueous barium hydroxide, followed by stirring at 60° C. under heating for 1 hour (to effect the hydrolytic ring-fission of the cyclic 2″,3″-carbamate moiety). The reaction solution was then neutralized by addition of carbon dioxide (Dry Ice) and the precipitate as deposited was filtered off. The filtrate was admixed with 10 mg of 5% palladium-on-carbon and then stirred at ambient temperature for 6 hours under a stream of hydrogen gas (to effect the removal of the amino-protecting benzyloxycarbonyl groups). The reaction mixture was filtered to remove the palladium catalyst, and the filtrate was passed through a column of 10 ml of a cation-exchange resin, Amberlite CG-50 ($NH_4^+$) for adsorption of the active product. The resin column was then washed with 30 ml of water and with 30 ml of 0.1N aqueous ammonia and subsequently eluted with 0.3N aqueous ammonia with collecting the eluate in 1-ml fractions. The fractions Nos. 3~8 were combined together and concentrated to dryness to afford 46 mg of a colorless powder of 5,2′,3′,4′,4″,6″-hexadeoxykanamycin (monocarbonate monohydrate). Yield 74%.

EXAMPLE 2

Synthesis of 1-N-[(S)-4-amino-2-hydroxybutyryl]-5,2′,3′,4′,4″,6″-hexadeoxykanamycin, namely the hexadeoxyamikacin.

(a) 5,2′,3′,4′,4″,6″-Hexadeoxykanamycin (40 mg; 0.085 milimoles) obtained in Example 1 as above was dissolved in 50 ml of a solution of 90% dimethylsulfoxide in water, to which was then added 109 mg (0.494 milimoles) of zinc acetate [$Zn(OOCCH_3)_2 \cdot 2H_2O$], followed by agitation at ambient temperature for 15 hours (for the formation of the complex of the hexadeoxykanamycin with zinc cations). The reaction mixture so obtained was admixed with 110 mg (0.402 milimoles) of benzyl S-4,6-dimethylpyrimid-2-ylthiocarbonate and stirred for 7 hours under heating to 50° C. (to effect the reaction of introducing the amino-protecting benzyloxycarbonyl groups).

To the resulting reaction solution was added 50 ml of ethyl ether to precipitate the N-protected product. This 3,6′,3″-tri-N-protected product was purified by column chromatography on silica gel (Wako Gel C-200, 20 g) developed with chloroform-methanol-conc. aqueous ammonia (20:10:1) with collecting the eluate in 4-ml fractions. The fractions Nos. 31~40 were combined together and concentrated to dryness to give 41 mg of 3,6′,3″-tris(N-benzyloxycarbonyl)-5,2′,3′,4′,4″,6″-hexadeoxykanamycin. Yield 61%.

(b) 3,6′,3″-Tris(N-benzyloxycarbonyl)-5,2′,3′,4′,4″,6″-hexadeoxykanamycin (35 mg; 0.044 milimoles) obtained in the above step (a) was dissolved in 5 ml of dimethylsulfoxide, to which were then added 0.01 ml (0.066 milimoles) of triethylamine and a solution of 22 mg (0.066 milimoles) of (S)-4-benzyloxycarbonylamino-2-hydroxybutyric acid N-hydroxysuccinimide ester in 1 ml of tetrahydrofuran. The resultant admixture was then agitated at ambient temperature for 4 hours (to effect the 1-N-acylation reaction). The reaction solution was admixed with 30 ml of water and extracted twice with 30 ml portions of ethyl acetate. The combined extract in ethyl acetate was dried over anhydrous sodium sulfate and concentrated to dryness, and the residue was purified by column chromatography on silica gel (Wako Gel C-200, 10 g) developed with chloroform-methanol (10:1) with collecting the eluate in 2-ml fractions. The fractions Nos. 37~44 were combined together and concentrated to dryness to give 34 mg of 3,6′,3″,4‴-tetrakis (N-benzyloxycarbonyl)hexadeoxyamikacin. Yield 76%.

(c) 3,6′,3″,4‴-Tetrakis(N-benzyloxycarbonyl) hexadeoxyamikacin (33 mg; 0.033 milimoles) obtained in the above step (d) was dissolved in a mixture of 5 ml of 50% aqueous methanol and 0.01 ml of acetic acid, to which was then added 3 mg of 5% palladium-on-carbon. The resultant admixture was stirred at ambient temperature for 7 hours under a stream of hydrogen gas (to effect the N-deprotecting reaction by the catalytic hydrogenolysis). The reaction mixture was filtered to remove the catalyst, and the filtrate was concentrated to dryness. The residue was taken up into 5 ml of water and the aqueous solution was passed through a column of 5 ml of a cation-exchange resin, Amberlite CG-50 ($NH_4^+$) for adsorption of the desired product. The resin column was washed with 15 ml of water with 10 ml of 0.2N aqueous ammonia and subsequently eluted with 0.5N aqueous ammonia with collecting the eluate in 0.5-ml fractions. The fractions Nos. 8~13 were combined together and concentrated to dryness to give 13 mg of a colorless powder of the hexadeoxyamikacin, namely 1-N-[(S)-4-amino-2-hydroxybutyryl]-5,2′,3′,4′,4″,6″-hexadeoxykanamycin (as the monocarbonate dihydrate). Yield 67%.

What we claim is:

1. A compound of the general formula (I)

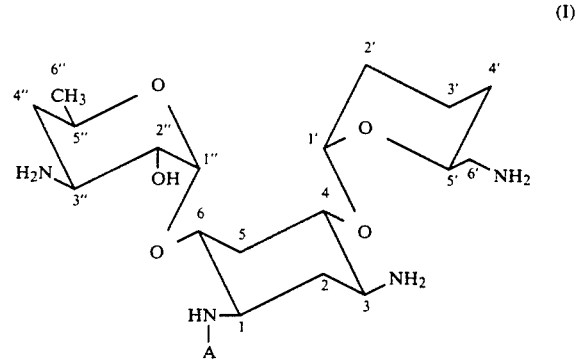

(I)

wherein A denotes a hydrogen atom or an (S)-4-amino-2-hydroxybutyryl group, or a pharmaceutically acceptable acid-addition salt thereof.

2. The compound of claim 1 which is 5,2′,3′,4′,4″,6″-hexadeoxykanamycin or a pharmaceutically acceptable acid-addition salt thereof.

3. The compound of claim 1 which is 1-N-[(S)-4-amino-2-hydroxybutyryl]-5,2′,3′,4′,4″,6″-hexadeoxykanamycin or a pharmaceutically acceptable acid-addition salt thereof.

4. A process for the production of 5,2′,3′,4′,4″,6″-hexadeoxykanamycin according to claim 1, which comprises the consecutive steps of:

(a) introducing an amino-protecting group each into the four amino groups of 3′,4′-dideoxykanamycin to prepare a tetra-N-protected derivative of 3′,4′-dideoxykanamycin represented by the formula (II)

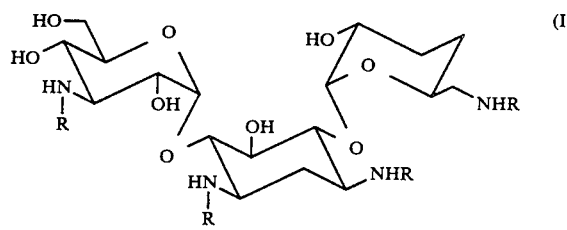

wherein R denotes an alkyloxycarbonyl group, a cycloalkyloxycarbonyl group or an aralkyloxycarbonyl group as an amino-protecting group of the formula

where B is an alkyl group of 1 to 4 carbon atoms, a cycloalkyl group of 3 to 6 carbon atoms or an aralkyl group, (b) reacting the tetra-N-protected 3',4'-dideoxykanamycin derivative of the formula (II) with a basic reagent in an anhydrous organic solvent to produce a cyclic 2",3"-carbamate derivative represented by the formula (III)

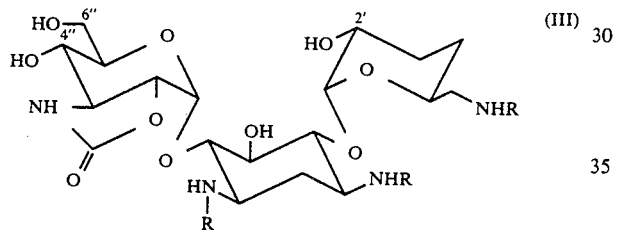

wherein R is the amino-protecting group as defined above, (c) reacting the cyclic 2",3"-carbamate derivative of the formula (III) with trifluoromethanesulfonyl chloride to sulfonylate the 2'-, 4"-, 6"-hydroxyl groups of the cyclic 2",3"-carbamate compound of the formula (III) and thereby produce the compound of the formula (IV)

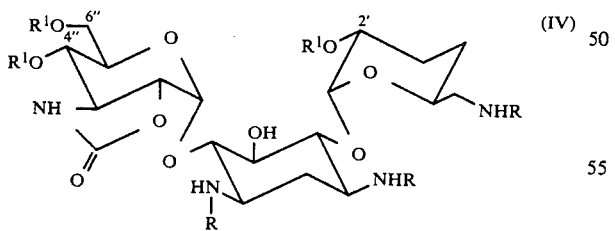

wherein R is the amino-protecting group as defined above and $R^1$ denotes a trifluoromethanesulfonyl group $-SO_2CF_3$, (d) reacting the compound of the formula (IV) with sodium thiophenolate to replace the 2'-, 4"- and 6"-trifluoromethanesulfonyloxy groups ($R^1O-$) of the compound of the formula (IV) each by a phenylthio group and thereby produce the compound of the formula (V)

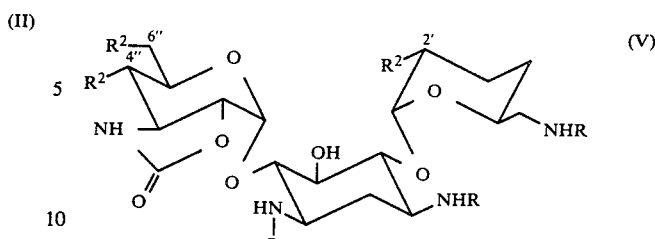

wherein R is the amino-protecting group as defined above and $R^2$ denotes a phenylthio group $-SC_6H_5$, (e) hydrogenolyzing the compound of formula (V) by reaction with Raney nickel in ethanol to replace the 2'-, 4"-, and 6"-phenylthio groups ($R^2$) each by a hydrogen atom and thereby produce the compound of the formula (VI)

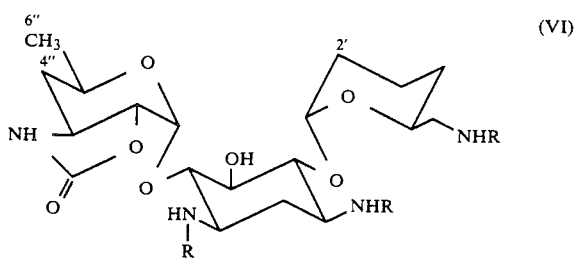

wherein R is the amino-protecting group as defined above, (f) reacting the compound of the formula (VI) with carbon disulfide, sodium hydroxide and methyl iodide to convert the 5-hydroxyl group of said compound (VI) into an S-methyldithiocarbonyloxy group and thereby produce a compound of the formula (VII)

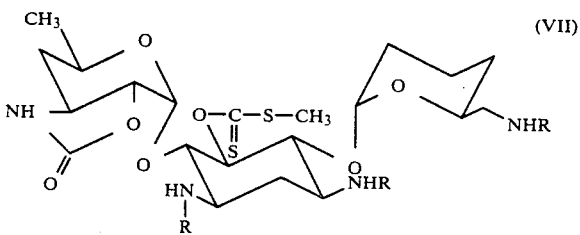

wherein R is the amino-protecting group as defined above, (g) hydrogenolyzing the 5-S-methyldithiocarbonylated compound of the formula (VII) by reaction with tributylstannane in the presence of $\alpha,\alpha'$-azobisisobutyronitrile to remove the 5-S-methyldithiocarbonyloxy group from the compound (VII) and thereby produce the 5-deoxygenated compound of the formula (VIII)

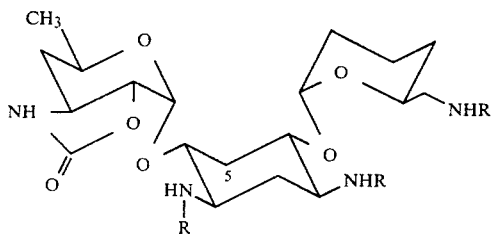

wherein R is the amino-protecting group as defined above.

(h) hydrolyzing the 5-deoxygenated compound of the formula (VIII) under alkaline conditions to fission the cyclic 2″,3″-carbamate ring of said compound and thereby produce the compound of the formula (IX)

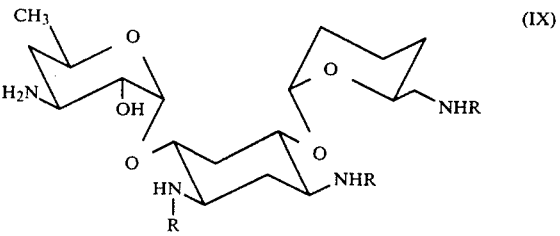

wherein R is the amino-protecting group as defined above, and (i) removing the amino-protecting groups (R) from the compound of the formula (IX) in a known manner to produce the 5,2′,3′,4′,4″,6″-hexadeoxykanamycin of the formula (Ia)

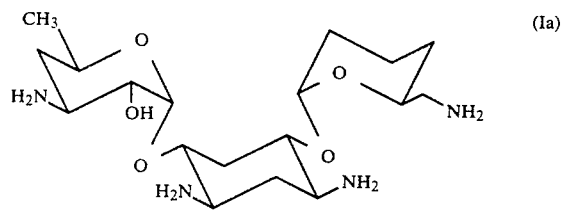

5. A process as claimed in claim 3 in which 1,3,6′,3″-tetrakis(N-benzyloxycarbonyl)-3′,4′-dideoxykanamycin is reacted with sodium hydride in the step (b) of the process to produce 1,3,6′-tris(N-benzyloxycarbonyl)-3′,4′-dideoxykanamycin 2″,3″-carbamate.

6. An antibacterial composition which comprises an antibacterially effective amount of 5,2′,3′,4′,4″,6″-hexadeoxykanamycin or 1-N-[(S)-4-amino-2-hydroxybutyryl]-5,2′,3′,4′,4″,6″-hexadeoxykanamycin or a pharmaceutically acceptable acid-addition salt thereof as defined in claim 1, in combination with a carrier for the active ingredient.

* * * * *